United States Patent [19]
Real

[11] Patent Number: 5,817,106
[45] Date of Patent: Oct. 6, 1998

[54] STEREOTACTIC GUIDE APPARATUS FOR USE WITH NEUROSURGICAL HEADFRAME

[76] Inventor: Douglas D. Real, 300 Girard Ave., Dothan, Ala. 36303

[21] Appl. No.: 857,406

[22] Filed: May 16, 1997

Related U.S. Application Data

[63] Continuation-in-part of Ser. No. 530,790, Sep. 19, 1995, Pat. No. 5,649,936.
[51] Int. Cl.⁶ .................................................. A61B 19/00
[52] U.S. Cl. ............................................................ 606/130
[58] Field of Search .................................. 606/53, 54, 59, 606/87, 86, 98, 129, 130

[56] References Cited

U.S. PATENT DOCUMENTS

| | | | |
|---|---|---|---|
| 4,350,159 | 9/1982 | Gouda | 606/130 |
| 4,638,796 | 1/1987 | Sheldon et al. | 606/130 |
| 4,706,665 | 11/1987 | Gouda | 606/130 |
| 5,280,427 | 1/1994 | Magnusson et al. | 361/413.01 |
| 5,618,288 | 4/1997 | Calvo | 606/130 |
| 5,643,286 | 7/1997 | Warner et al. | 606/130 |

*Primary Examiner*—Michael Powell Buiz
*Assistant Examiner*—David O. Reip
*Attorney, Agent, or Firm*—Jones & Askew, LLP

[57] ABSTRACT

A stereotactic guide apparatus is disclosed for positioning a surgical instrument along three axes. The disclosed stereotactic guide apparatus is adapted for use in neurosurgical procedures in conjunction with a conventional headframe mounted to a patient's skull and having an arc extending above and across the skull. A platform is mounted to the arc of the headframe. An X-slide is mounted to the platform for movement along the X-axis. A Y-slide is mounted to the X-slide for movement along the Y-axis. A Z-stage is mounted to the Y-slide. By moving the X-slide and Y-slide, the Z-stage is thus positionable along both the X- and Y-axes. The Z-stage includes an instrument slide mounted for movement along the Z-axis. A surgical instrument such as an electrode, injection cannula, or biopsy needle can be mounted to the instrument slide for movement of the instrument along the Z-axis.

7 Claims, 14 Drawing Sheets

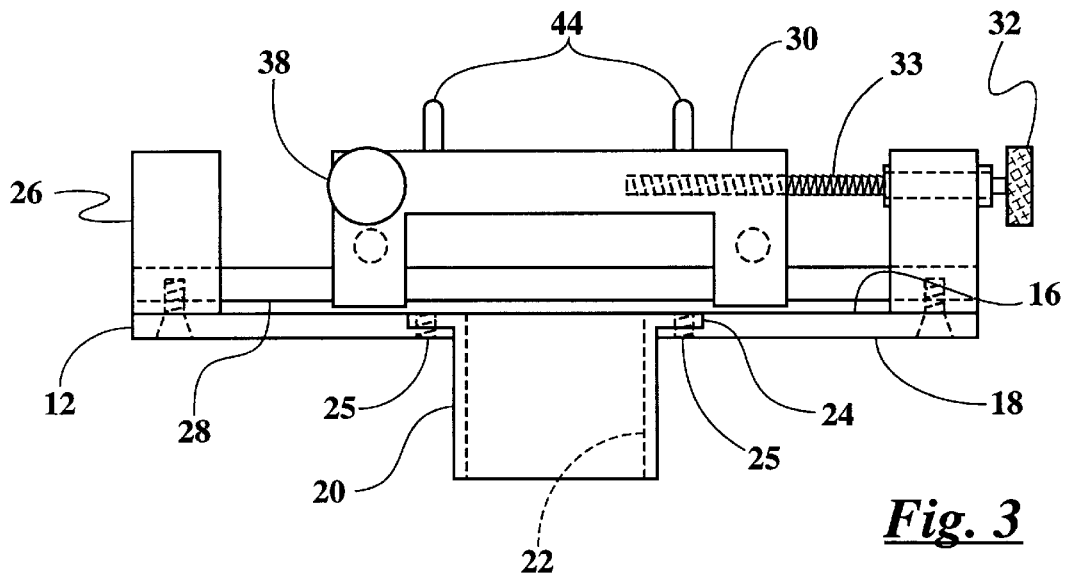
Fig. 3
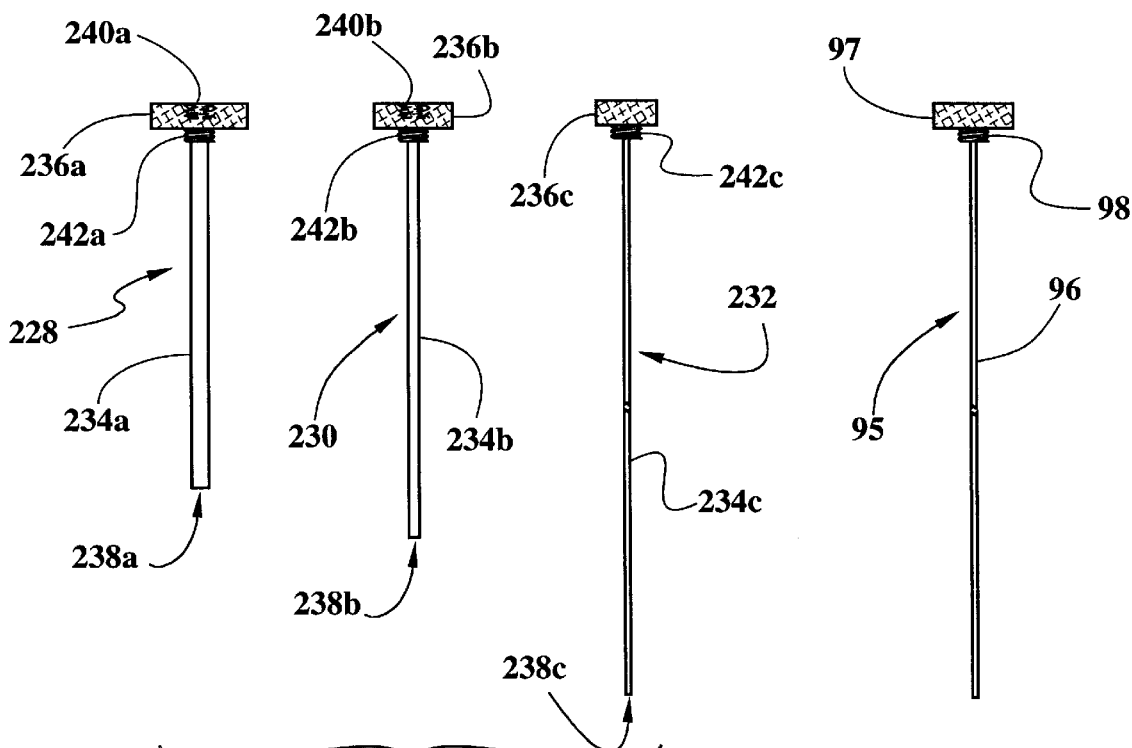
Fig. 4
Fig. 16

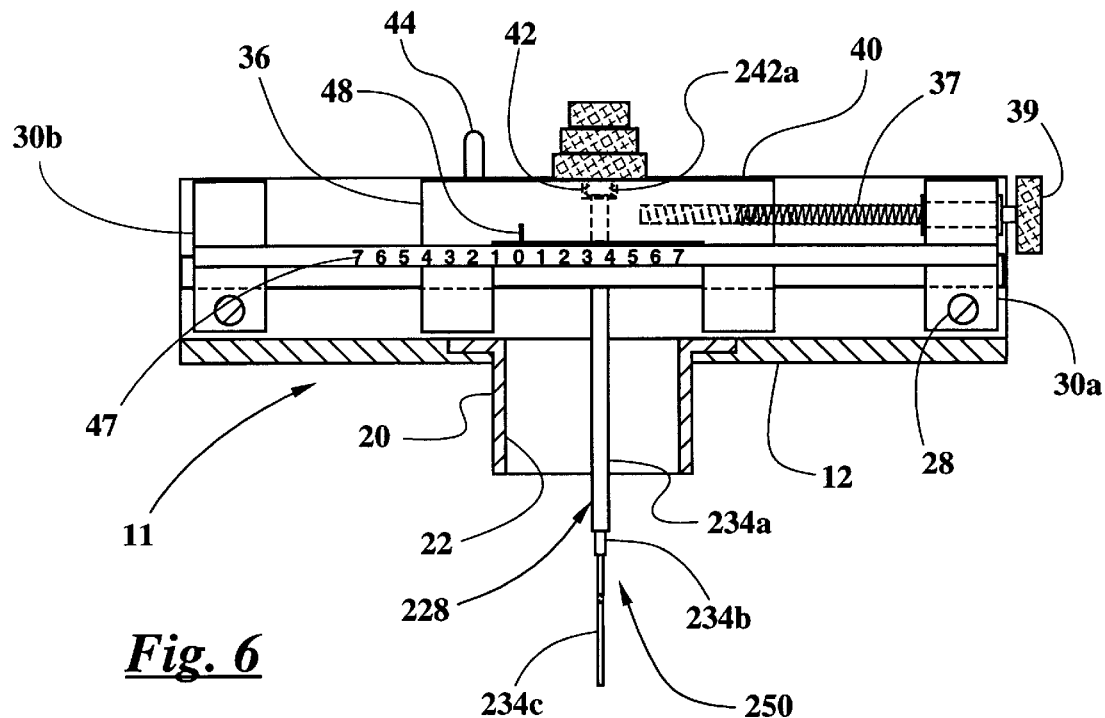
*Fig. 6*
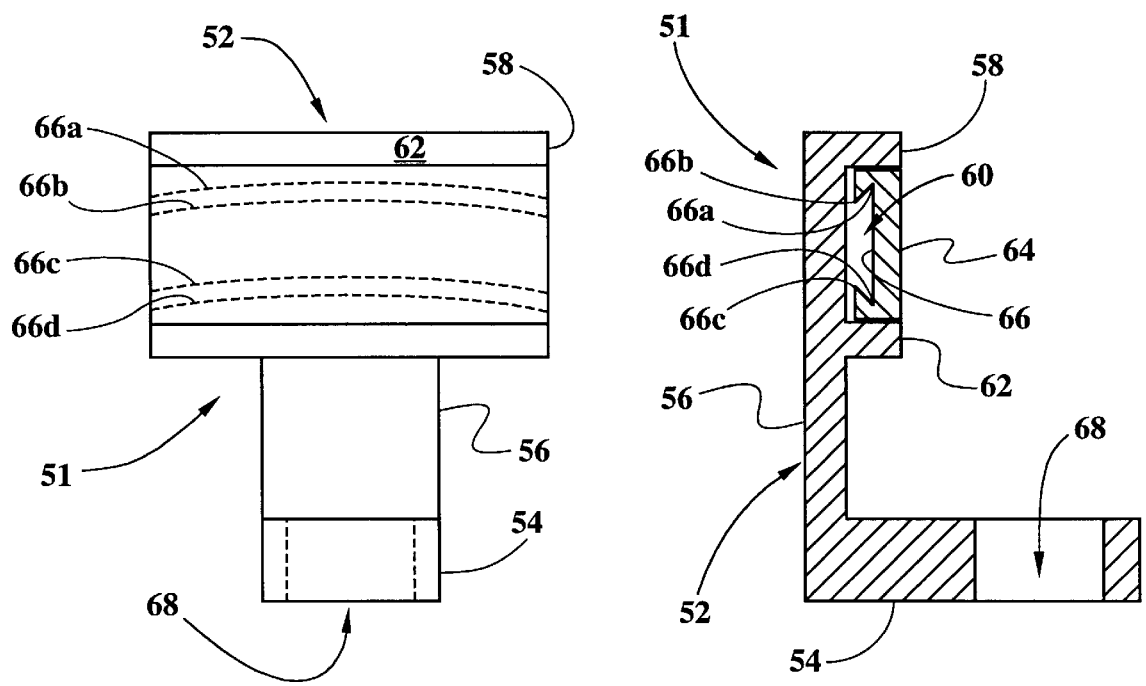
*Fig. 8*          *Fig. 9*

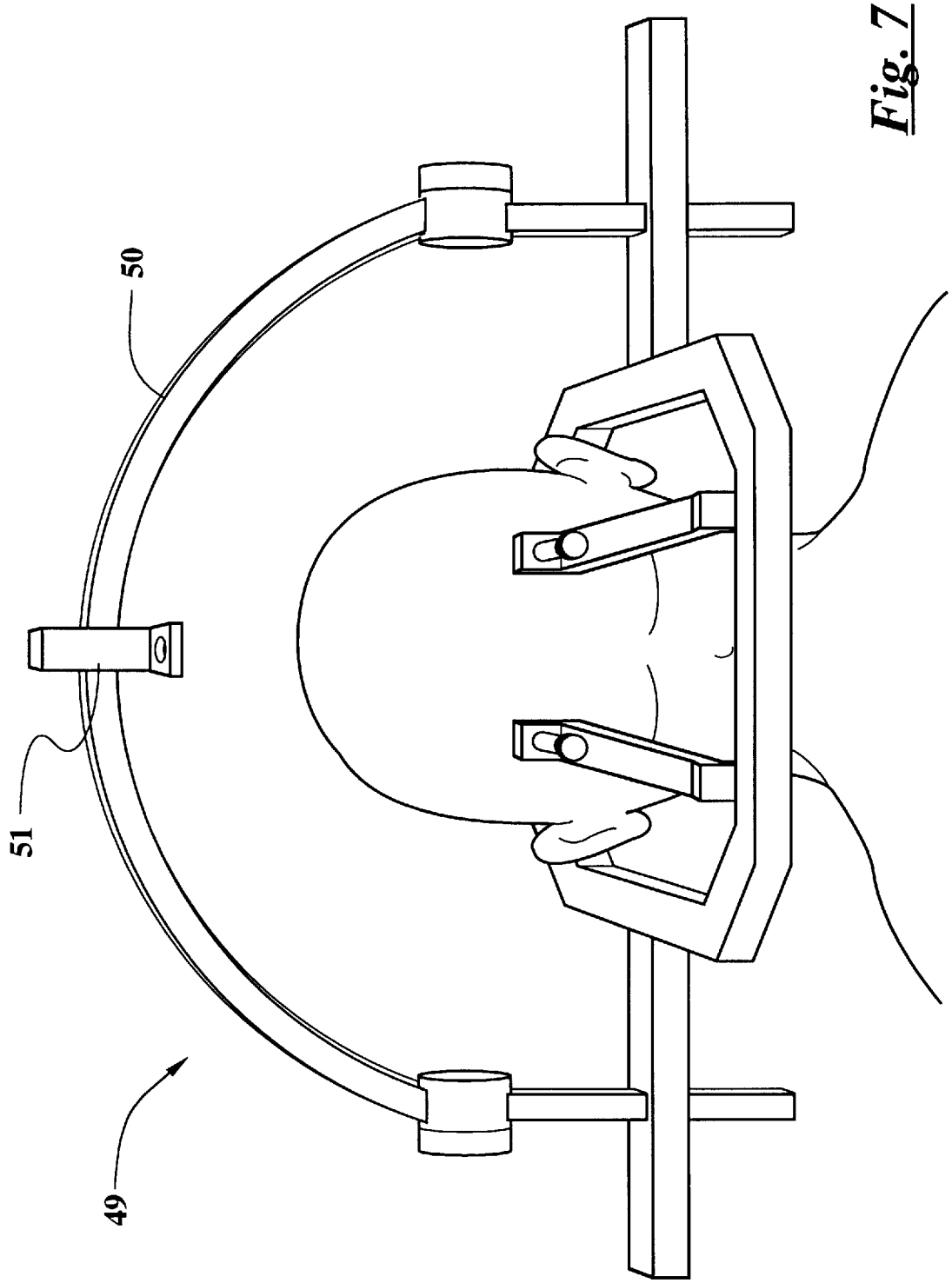

STEREOTACTIC GUIDE APPARATUS FOR USE WITH NEUROSURGICAL HEADFRAME

CROSS-REFERENCE TO RELATED APPLICATION

This application is a continuation-in-part of U.S. patent application Ser. No. 08/530,790, now U.S. Pat. No. 5,649,936 filed Sep. 18, 1995.

TECHNICAL FIELD

The present invention relates generally to a stereotactic guide apparatus for neurosurgery, and relates more specifically to a stereotactic guide apparatus which removably mounts to a neurosurgical headframe and provides three-dimensional control guidance of an instrument.

BACKGROUND OF THE INVENTION

Headframes for stereotactic neurosurgery are well known. These headframes are ring-shaped structures which are mounted to the skull of a patient to provide a fixed reference with respect to the patient's brain. An arcuate rail has its opposite ends fastened to opposing sides of the headframe and extends above and across the patient's skull. A guide is movably mounted on the rail and can be positioned at any suitable location along the length of the rail to serve as a guide for surgical instruments. Such headframes are commonly used for brain biopsies, tumor removal, or any other modality of deep brain surgery where the surgeon requires guidance to properly position an instrument. In addition, such headframes are useful for cryosurgical treatment of Parkinson's disease, epilepsy, microelectrode guidance, brain nuclei and mapping, placement, positioning, neuronal micro stimulation, recording, lesioning, resection, localization of brain nuclei, microinjection cannula system, micro injection of drugs, donor human tissue, and the like.

Although a substantial advance over unguided neurosurgery, prior art headframes have significant drawbacks. While the guide can be repositioned to any other location along the plane of the rail, the guide cannot be repositioned transverse to the plane of the rail without removing the headframe from the patient, rotating the headframe so that the plane of the rail passes through the new location, and then remounting the headframe to the patient's skull. Moving the headframe in this manner is too time consuming and too inaccurate.

Thus there is a need for a stereotactic guide apparatus for use with a neurosurgical headframe which permits a tool to be repositioned along any of three axes without having to remove the headframe from the patient.

Another difficulty associated with use of prior art tool guides used with conventional headframes for neurosurgery do not provide adequate control and precision over the positioning of a tool. Since such tool guides are used to position surgical instruments within the brain of a patient, precise control and accuracy are of paramount importance. Thus there is a need for a stereotactic guide apparatus for use with a neurosurgical headframe which provides guidance for a surgical instrument with greater precision and control than heretofore possible.

SUMMARY OF THE INVENTION

Stated generally, the present invention comprises a stereotactic guide and headstage apparatus that is adapted for localizing on any portion of the brain, with maximum accuracy and a positive finite degree. This stereotactic guide apparatus can be used for brain mapping such as for the treatment of Parkinson's disease, deep seated brain tumors, hyperkinetic disorders, various maladies of the human brain, and the like.

Stated somewhat more specifically, the present invention comprises an stereotactic guide apparatus for use with neurosurgical headframe which has an arc extending above and across the skull of a patient to whom the headframe is mounted and a slide mounted for sliding movement along the arc. The stereotactic guide apparatus includes a platform defining a plane and X, Y, and Z axes. Means are provided for mounting the platform to the slide on the arc of the headframe. An X-slide is movably supported on the platform for movement along the X-axis, and a Y-slide is movably supported on the X-slide for movement along the Y-axis. A tubular instrument guide is mounted to the Y-slide and extends parallel to the Z-axis. A surgical instrument can be advanced through the tubular instrument guide, and the X-slide and the Y-slide can be moved to position the surgical instrument with respect to the X and Y axes.

In a preferred embodiment the stereotactic guide apparatus further includes a Z-stage. The Z-stage comprises a base which is mounted to the Y-slide. A Z-axis support means is mounted to the Z-stage base and extends parallel to the Z-axis. An instrument slide is movably mounted to the Z-axis support means for movement parallel to the Z-axis. An instrument attachment means is operatively associated with the instrument slide for attaching a surgical instrument to the instrument slide. The instrument attachment means and the instrument slide are arranged such that when a surgical instrument is attached to the instrument slide and the instrument slide is moved along the Z-axis support means, the surgical instrument is advanced through the tubular instrument guide.

In another aspect, the present invention pertains to a novel electrode especially adapted for use in mapping brain activity. The electrode includes an elongated hollow shaft comprised of an electrically conductive material. An electrode wire comprised of an electrically conductive material is mounted within a forward end of the elongated hollow shaft in electrically conductive communication with the shaft and extending forward from the forward end of the shaft. A glass tip encapsulates the forward end of the elongated hollow shaft and the electrode wire projecting therefrom. In a preferred embodiment, a tube of electrically insulating material is disposed around the elongated hollow shaft, a forward end of the tube being bonded to a rearward portion of the glass tip.

Accordingly, it is an object of the present invention to provide for a stereotactic guide and headstage apparatus that can be utilized successfully for any stereotactic neurosurgery, functional neurosurgery, deep brain microstimulation, brain mapping, and treating Parkinson's disease, epilepsy, sleep disorders, and movement disorders.

Still another object of the present invention is to provide a stereotactic guide and headstage apparatus which will overcome the deficiencies, drawbacks, and disadvantages of conventional stereotactic guide apparatus, transplant devices, or method thereof.

Yet another object of the present invention is to provide an apparatus which will accurately, precisely locate a target area in the brain of a patient, penetrate the brain, utilizing the cannula and stylet assembly, and enabling the precise activity on the target area (i.e. donor tissue transplant, brain nuclei, micro-stimulations, localization, etc.) while minimizing trauma or damage to the recipient brain tissue.

It is yet another object of the present invention to provide for a stereotactic guide and headstage apparatus which includes a Z-stage for permitting movement along the Z-axis of the Z-direction.

Still another object of the present invention is to provide a Z-stage that is adapted to be removably secured to an XY-stage.

Another object of the present invention is to provide a Z-stage which includes a means of accepting and maintaining a carrier tube assembly for enabling successful insertion of a microelectrode into the brain of a patient.

A further object of the present invention is to provide for a stereotactic guide and headstage apparatus which includes an interlocking cannula and stylet system for electrode guidance to permit utilization of transplant cannulae, stimulation implants, and micro and macro electrodes.

It is still a further object of the present invention to provide for a stereotactic guide and headstage apparatus which will provide for precise localization of tumors, lesion, abnormalities and the like.

Yet another object of the present invention, to be specifically enumerated herein, is to provide a stereotactic guide and headstage apparatus in accordance with the preceding objects and which will be of easy and efficient to be utilized so as to provide an apparatus that would be economically feasible, long lasting and relatively trouble free in operation.

Other objects, features, and advantages of the present invention will become apparent upon reading the following specification, when taken in conjunction with the drawings and the appended claims.

BRIEF DESCRIPTION OF THE DRAWINGS

FIG. 3 is a side view of the XY-stage of FIG. 1.

FIG. 4 is a side view of an outer guide tube, an inner guide tube, and a stylet.

FIG. 6 is a cutaway view of the XY-stage as seen along line 6—6 of FIG. 1 with the guide tube assembly of FIG. 5 mounted thereto.

FIG. 7 is a perspective view of a prior art neurosurgical headframe of a general type with which the stereotactic guide apparatus of the present invention is adapted to be used.

FIG. 8 is a front view of an arc slide for use on the neurosurgical headframe of FIG. 7.

FIG. 9 is a side cross-sectional view of the arc slide of FIG. 8.

FIG. 16 is a side view of a carrier tube which is used with the Z-stage of FIGS. 10–13.

DETAILED DESCRIPTION OF THE DISCLOSED EMBODIMENT

Figure 1:
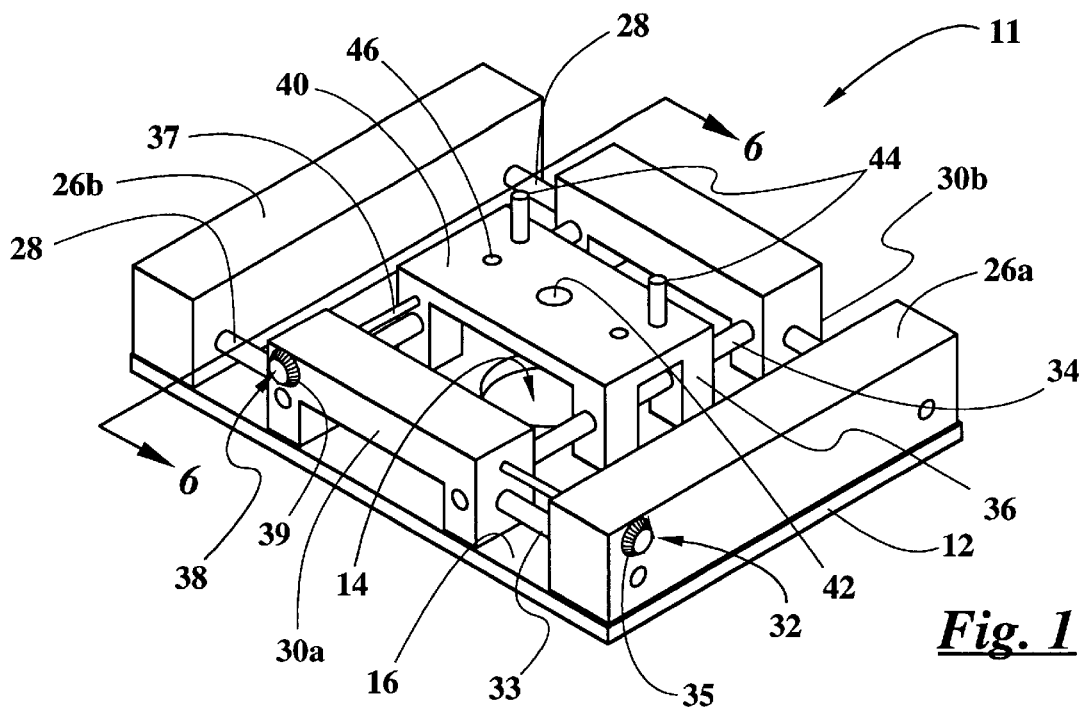
FIG. 1 is an isometric view of an XY-stage of a stereotactic guide apparatus according to the present invention.
Figure 2:
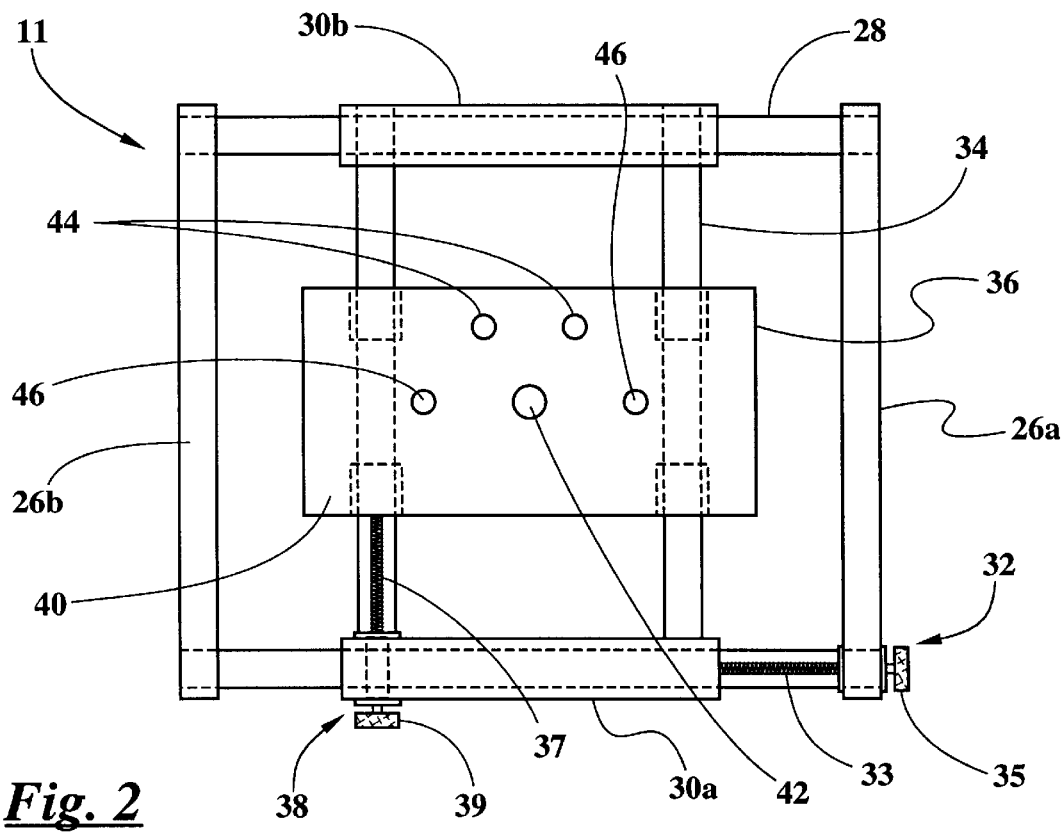
FIG. 2 is a top view of the XY-stage of FIG. 1.

Referring now to the drawings, in which like numerals indicate like elements throughout the several views, the drawing figures illustrate various views of a stereotactic guide apparatus 10 of the present invention. Referring first to FIGS. 1 and 2, an XY-stage 11 of the stereotactic guide apparatus 10 is depicted. The XY-stage 11 includes a base member 12. For ease of description, X and Y axes are designated by the arrows 13. A round hole 14 is located in the center of the base member 12. A pair of support blocks 26a, 26b is located on the top surface 16 of the base member 12 along opposite edges thereof.

Extending between the supports 26a, 26b adjacent the remaining two edges of the base 12 is a pair of parallel, spaced-apart, horizontal medial slide support rods 28. A pair of medial/lateral slides, or "X-slides" 30a, 30b are slidably disposed one on each of the medial slide supports 28. A medial movement mechanism 32 is operatively connected to the X-slide 30a for effecting movement of the X-slide 30a in the medial/lateral direction, or X-direction. The medial movement mechanism 32 comprises a threaded rod 33 which is inserted through a smooth bore in the support 26a and is threadably received within a corresponding threaded bore in the adjacent end of the X-slide 30a. Turning the threaded rod 33, advantageously by means of a knurled thumbscrew 35 at the head of the rod, moves the X-slide 30a toward or away from the support 26a.

Extending perpendicularly between the X-slides 30a, 30b is an anterior slide support means comprising a pair of parallel, spaced-apart anterior slide support tracks 34. Suspended on the anterior slide support tracks 34 is an anterior/posterior slide, or "Y-slide" 36. The Y-slide 36 includes a top panel 40 having a central threaded aperture 42. A pair of upstanding pins 44 project upward from the top panel 40 adjacent a longitudinal edge thereof and spaced equidistant from the central aperture 42. In addition, a pair of threaded holes 46 are formed in the upper surface of the platform 40.

The XY-stage 11 further includes an anterior movement mechanism 38 operatively connected to the Y-slide 36 for effecting movement of the Y-slide in the anterior/posterior direction, or Y-direction. The anterior movement mechanism 38 comprises a threaded rod 37 which is inserted through a smooth bore in the X-slide 30a and is threadably received within a corresponding threaded bore in the adjacent end of the Y-slide 36. Turning the threaded rod 37, advantageously by means of a knurled thumbscrew 39 at the head of the rod, moves the Y-slide 36 toward or away from the X-slide 30a.

It will be appreciated that the pair of X-slides 30a, 30b is linked together by the anterior slide support tracks 34. Accordingly, when the threaded rod 33 is turned to move the first X-slide 30a along the X-axis, the second X-slide 30b is also displaced toward or away from the support 26a.

Referring now to FIG. 3, a tubular mounting adapter 20 is positioned within the round hole 14 in the base member 12 of the XY-stage. The mounting adapter 20 includes a hollow cylindrical body 22 and has a flange 24 located at its upper end. The lower surface of the flange 24 bears against the upper surface 16 of the base member 12 when the bushing is properly seated within the round hole 14 in the base member. The mounting adapter 20 is then secured to the base member 12 by means of threaded fasteners 25 which pass through the flange 24 of the mounting adapter and engage the base member.

FIG. 4 shows an outer guide tube 228, an inner guide tube 230, and a stylet or occluder 232. The outer guide tube 228 includes a hollow shaft 234a having a bore 238a. In the disclosed embodiment the shaft 234a of the outer guide tube 228 is approximately 90 millimeters in length. The outer guide tube 228 further comprises a cap 236a having an internally threaded bore 240a. Located beneath the cap 236a of the outer guide tube 228 is an externally threaded collar 242a.

The inner guide tube 230 includes a hollow shaft 234b having a bore 238b. The diameter of the shaft 234b of the inner guide tube 230 is sized to fit within the bore 238a of the shaft 234a of the outer guide tube. In the disclosed embodiment the shaft 234b is approximately 150 millimeters in length. The inner guide tube 230 further includes a cap 236b having an internally threaded bore 240b. Located beneath the cap 236b of the inner guide tube 230 is an externally threaded collar 242b.

The stylet 232 includes a solid shaft 234c and a cap 236c. The diameter of the shaft 234c of the stylet 232 is sized to fit within the bore 238b of the shaft 234b of the inner guide tube 230. In the disclosed embodiment the shaft 234c is approximately 150 millimeters in length. An externally threaded collar 242c is located beneath the cap 236c.

Figure 5:
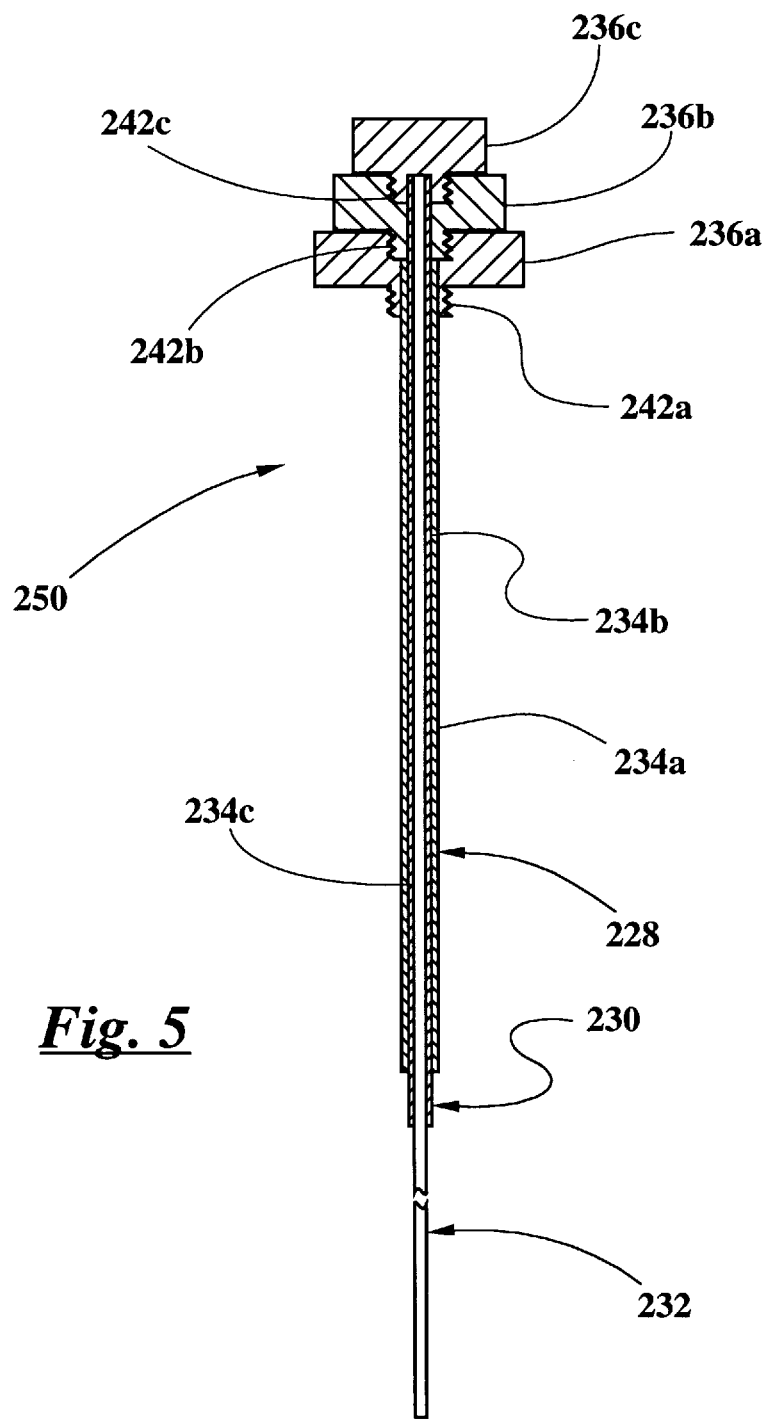
FIG. 5 is a cross-sectional view of a guide tube assembly comprising the outer and inner guide tubes and the stylet of FIG. 4.
Figure 10:
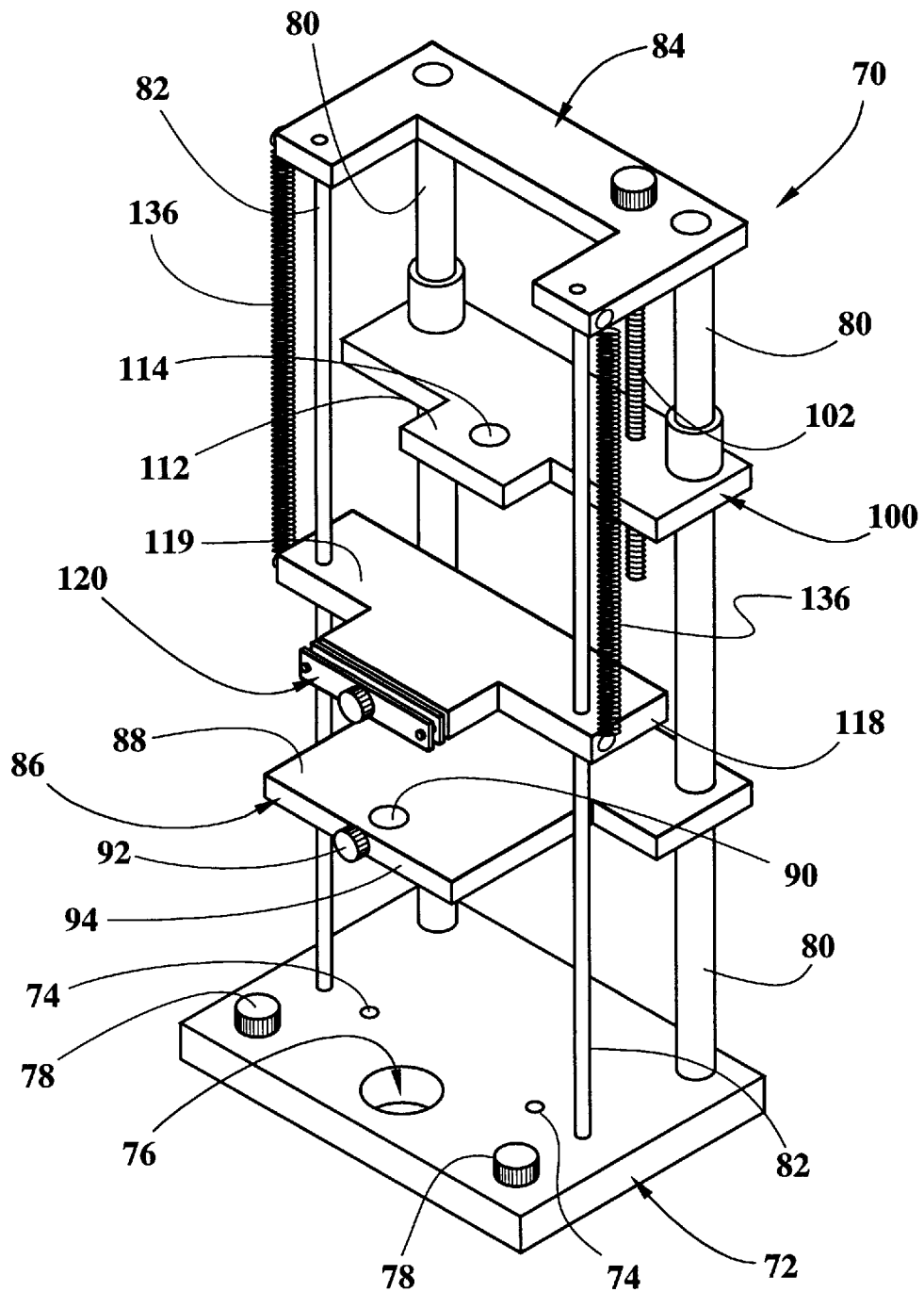
FIG. 10 is a perspective view of a Z-stage component of the stereotactic guide apparatus of the present invention.

FIG. 5 shows a guide tube assembly 250 comprising the outer guide tube 228, the inner guide tube 230, and the stylet 232. The shaft 234b of the inner guide tube 230 is inserted into the upper end of the outer guide tube 228 and advanced until the externally threaded collar 242b of the inner guide tube engages the internal threads 240a of the outer guide tube. Turning the inner guide tube 230 relative to the outer guide tube 228 will engage the threaded collar 242b of the inner guide tube with the threads 240a of the outer guide tube to couple the inner and outer guide tubes together. Similarly the shaft 234c of the stylet 232 is inserted into the upper end of the inner guide tube 230, and the externally threaded collar 242c of the stylet engage the internal threads 240b of the inner guide tube 230 to couple the stylet 232 and the inner guide tube 230 together.

Because of the relative lengths of the shafts 234a, 234b, and 234c, when the outer guide tube 228, inner guide tube 230, and stylet 232 of the disclosed embodiment are assembled into the guide tube assembly 250, the shaft 234b of the inner guide tube 230 projects approximately 60 millimeters beyond the end of the outer guide tube 228, and the forward end of the solid shaft 234c of the stylet 232 extends just slightly beyond the end of the shaft 234b of the inner guide tube 230.

FIG. 6 shows the guide tube assembly 250 assembled onto the XY-stage 11. The externally threaded collar 242a of the outer guide tube 228 is threaded into the threaded aperture 42 in the center of the top panel 40 of the Y-slide 36. The shafts 234a, 234b, and 234c of the outer guide tube 228, inner guide tube 230, and stylet 232 respectively extend downward through the hollow cylindrical body 22 of the mounting adapter 20.

Also shown in FIG. 6 is a scale 47 extending between corresponding ends of the X-slides 30a, 30b. The scale 47 includes markings in one millimeter increments. A reference mark 48 on the Y-slide 36 identifies a corresponding one of the incremental markings to indicate the displacement of the needle assembly 250 from center in the direction of the Y-axis. A similar scale (not shown) is provided extending between corresponding ends of the supports 26a, 26b, and a reference mark along an edge of the X-slide 30b indicates the displacement of the needle assembly 250 in the X-direction.

FIG. 7 depicts a conventional prior art neurosurgical headframe 49 of the general type with which the stereotactic guide apparatus 10 of the present invention is adapted to be used. The headframe 49 illustrated in FIG. 7 is manufactured by CRW and Elekta, though it will be understood that the headframe 49 is only illustrative of a headframe with which the stereotactic guide apparatus 10 can be used and is by no means intended to limit the invention. The headframe 49 is mounted to the skull of a patient in a conventional manner and includes an arc 50 which extends above and across the patient's skull in spaced-apart relation thereto. An arc slide 51 is slidably mounted to the arc 50 for movement thereon.

Referring now to FIGS. 8 and 9, the arc slide 51 comprises a bracket member 52 which is L-shaped in cross-section. The bracket member 52 comprises a base 54, an upstanding leg 56, and a head portion 58. A circular bore 68 is formed through the base 54 of the bracket member 52. A horizontal, rectangular channel 60 is formed in the forward face 62 of the head portion 58. A block 64 is positioned within the channel 60 and has an arcuate track 66 formed on its interior surface. The track 66 on the interior surface of the block 64 is dovetail-shaped in cross-section and has edges 66a, 66b, 66c, and 66d. The track 66 receives the arc 50 of the headframe 49 therewithin. The block 64 is secured within the channel 60 of the bracket member 52, such as by an interference fit or by threaded fasteners (not shown), thereby coupling the arc slide 51 to the arc 50 of the headframe assembly 49.

Referring now to FIGS. 10–13, the stereotactic guide apparatus 10 further comprises a Z-stage 70, which is adapted to be removably secured to the XY-stage 11. The Z-stage 70 comprises a base 72 having a pair of alignment holes 74 formed therein. The alignment holes 74 are located and sized to receive the upstanding pins 44 projecting upward from the top panel 40 of the Y-slide 36. The base 72 of the Z-stage 70 further comprises a circular opening 76 which is located and sized to correspond to the central aperture 42 of the top panel 40 of the Y-slide 36 when the base 72 is mounted to the Y-slide. The base 72 of the Z-stage 70 further comprises a pair of securing screws 78 received within threaded bores of the base 72, which are located and configured to engage the threaded holes 46 in the upper surface of the platform 40 of the Y-slide 36 to secure the base 72 of the Z-stage 70 to the Y-slide. Because the arrangement of the upstanding pins 44 and the threaded holes 46 of the XY-stage 11 is asymmetrical, the Z-stage 70 cannot be accidentally installed onto the XY-stage improperly.

The Z-stage 70 further comprises a pair of upstanding main support rods 80 and a pair of electrode slide rods 82 projecting upward from the base 72. A substantially U-shaped top plate 84 is mounted to the upper ends of the rods 80, 82. A carrier tube holder 86 is fixedly mounted to the main support rods 80 at a location spaced upward from the base 72 by a distance of approximately one-third the height of the main support rods 80. The carrier tube holder 86 is essentially T-shaped and includes a forward projecting leg 88. A circular opening 90 is formed in the forward projecting leg 88 of the carrier tube holder 86 adjacent its forward end. The circular opening 90 is dimensioned to receive the shaft and collar of the carrier tube therethrough. A thumb screw 92 threadably mounted in the forward edge 94 of the carrier tube holder 86 has its tip extending radially into the circular opening 90.

The carrier tube holder 86 is adapted to support a carrier tube 95, which is illustrated in FIG. 16. The carrier tube 95 comprises a hollow tubular shaft 96, a head 97 located at the upper end of the shaft, and an annular collar 98 located immediately below the head 97. The shaft 96 of the carrier tube 95 of the disclosed embodiment has a diameter sized such that the shaft of the carrier tube can be received within the bore 234b of the inner guide tube 230. The shaft 96 of the carrier tube 95 is approximately 180 millimeters in length. The head 97 of the carrier tube 95 is larger than the circular opening 90 in the carrier tube holder 86, and the collar 98 is dimensioned to be received snugly within the circular opening 90.

Figure 13:
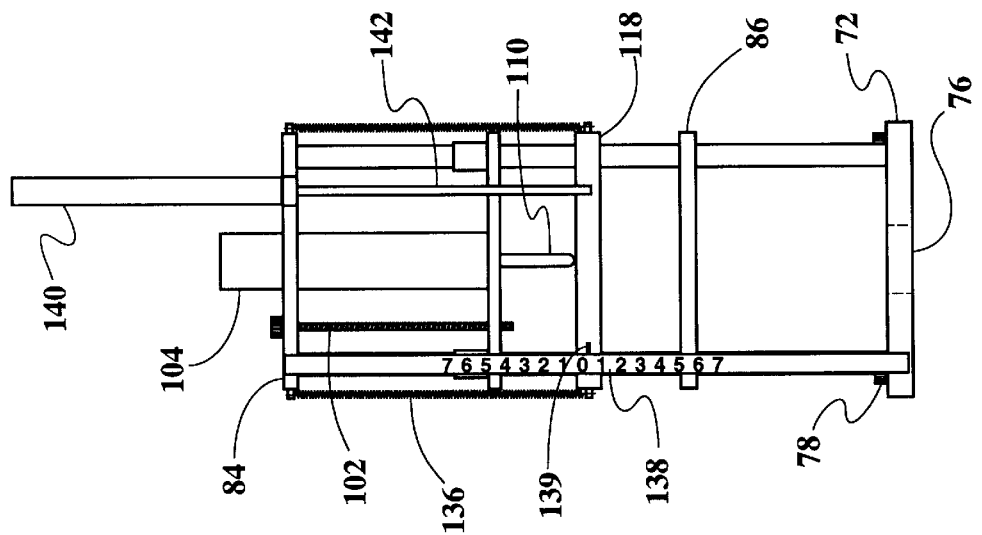
FIG. 13 is a rear elevation view of the Z-stage component of FIG. 10.
Figure 12:
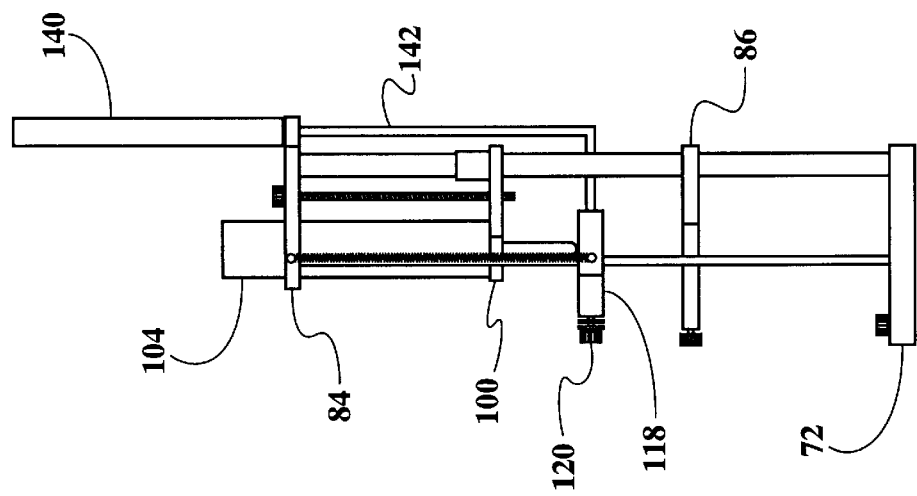
FIG. 12 is a side elevation view of the Z-stage component of FIG. 10.
Figure 11:
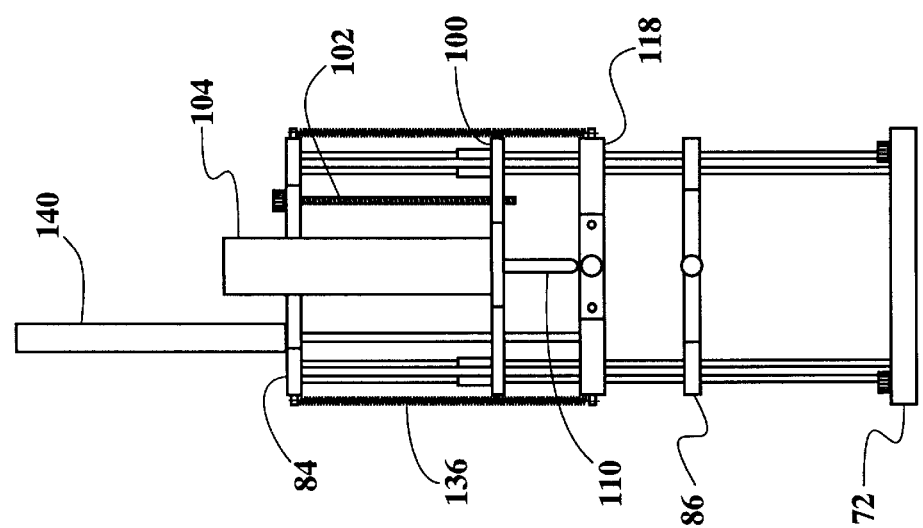
FIG. 11 is a front elevation view of the Z-stage component of FIG. 10.

FIGS. 11–13 show the assembled Z-stage 70 with the carrier tube 95 installed onto the carrier tube holder 86. The carrier tube 95 is positioned onto the carrier tube holder 86 with the annular collar 98 of the carrier tube disposed within the circular opening 90 of the carrier tube holder 86, the lower end of the cap 97 resting on the upper surface of the carrier tube holder 86, and the shaft 96 of the carrier tube 95 extending downward from the carrier tube holder. When the carrier tube 95 is thus positioned, the thumb screw 92 on the carrier tube holder 86 is tightened to secure the carrier tube to the carrier tube holder.

Referring again to FIGS. 10–13, a coarse drive slide 100 is slidably mounted on the main support rods 80 between the top plate 84 and the carrier tube holder 86. The coarse drive slide 100 is a planar, generally T-shaped member and includes a forward projecting leg 112. A threaded bore 114 is formed in the forward projecting leg 112. A threaded coarse drive screw 102 extends downward through a clear bore in the top plate 84 and engages a threaded bore in the coarse drive slide 100, such that rotating the coarse drive screw 102 will cause the coarse drive slide 100 to raise or lower. The purpose of the coarse drive screw 102 is twofold: first, to permit movement of the coarse drive slide 100 to a location such that the target tissue is within the range of movement of a microdrive system (described below); and second, to permit manual adjustment of the coarse drive slide if the physician so chooses or to permit the surgical instrument to be withdrawn from the patient's brain in the event of a power failure or the like.

Figure 14:
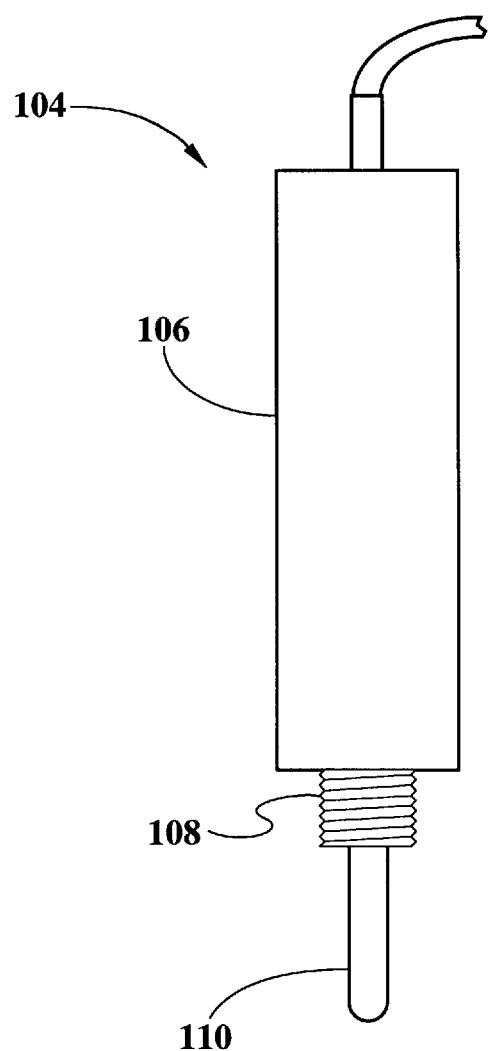
FIG. 14 is a schematic representation of a microdrive unit of the general type used with the stereotactic guide apparatus of the present invention.

FIG. 14 illustrates a conventional microdrive unit 104 of a general type used with the stereotactic guide apparatus 10 of the present invention. The microdrive unit 104 comprises a cylindrical housing 106 having an externally threaded collar 108 located at its forward end. A push rod 110 extends through the collar 108 and projects from the forward end of the housing 106. As shown in FIGS. 11–13, the microdrive unit 104 is mounted to the coarse drive slide 100 of the Z-stage 70 by threading the externally threaded collar 108 into the threaded bore 114. When the microdrive unit 104 is energized, a screw drive mechanism located within the housing 106 extends or retracts the push rod 110.

Figure 15:
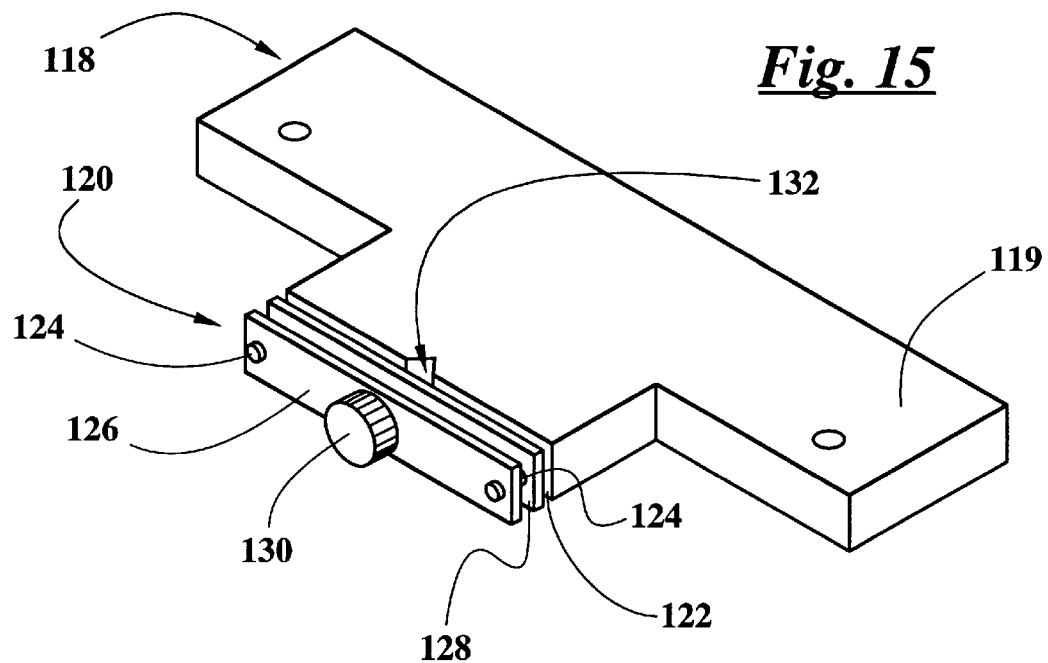
FIG. 15 is an enlarged view of a front portion of an electrode slide of the Z-stage component of FIGS. 10–13.

Referring again to FIGS. 10–13, an electrode slide 118 is slidably mounted on the electrode slide rods 82. The electrode slide 118 has an upper surface 119 and has an electrode holder assembly 120 located at its forward edge 122. As can be seen in the enlarged view of FIG. 15, a pair of support rods 124 project forward from the forward edge 122 of the electrode slide 118. A thumb screw support plate 126 is fixedly mounted to the forward ends of the support rods 124. An electrode holder pressure plate 128 is slidably mounted on the support rods 124 between the thumb screw support plate 126 and the forward edge of the electrode slide 118. A thumb screw 130 is threaded through the thumb screw support plate 126 so that its tip bears against the electrode holder pressure plate 128. A vertical notch 132 is formed in the center of the forward edge 122 of the electrode slide 118. To mount an electrode to the electrode slide 118, the electrode is fed downward between the electrode holder pressure plate 128 and the forward edge of the electrode slide 118. The shaft of the electrode is positioned within the notch 132 to align the electrode vertically with respect to the electrode slide 118. The thumb screw 130 is then tightened, causing the electrode holder pressure plate 128 to clamp the electrode against the forward edge 122 of the electrode slide 118.

Still referring to FIGS. 10–13, a pair of slide return springs 136 have their upper ends attached to the top plate 84 and their lower ends attached to the electrode slide 118 to bias the electrode slide 118 upward. When the push rod 110 of the microdrive unit 104 is actuated to extend downward, the push rod 110 bears against the upper surface 119 of the electrode slide 118 to bias the electrode slide downward. When the microdrive unit 104 is activated to retract the push rod 110, the slide return springs 136 bias the electrode slide 118 upward. In this manner, the electrode slide 118 moves in response to the microdrive unit 104.

Referring now to FIG. 13, two different means are illustrated for tracking the position of the electrode slide 118. For visually tracking the position of the electrode slide 118, a scale 138 is provided on the rear of the Z-stage 70 extending between the base 72 and the top plate 84. A pointer 139 is inscribed on the adjacent side of the electrode slide 118 to indicate the displacement of the electrode slide in the Z-direction. For electronically tracking the position of the electrode slide 118, a linear potentiometer 140 is provided. The linear potentiometer 140 is mounted to the top plate 84 and has a potentiometer push rod 142 extending from its lower end. The lower end of the push rod 142 is coupled to the electrode slide 118. In the case of both visual and electronic tracking, the position of the electrode slide 118 is directly measured, whether the electrode slide is moved by way of the coarse drive 102 or the microdrive 104.

Figure 17:
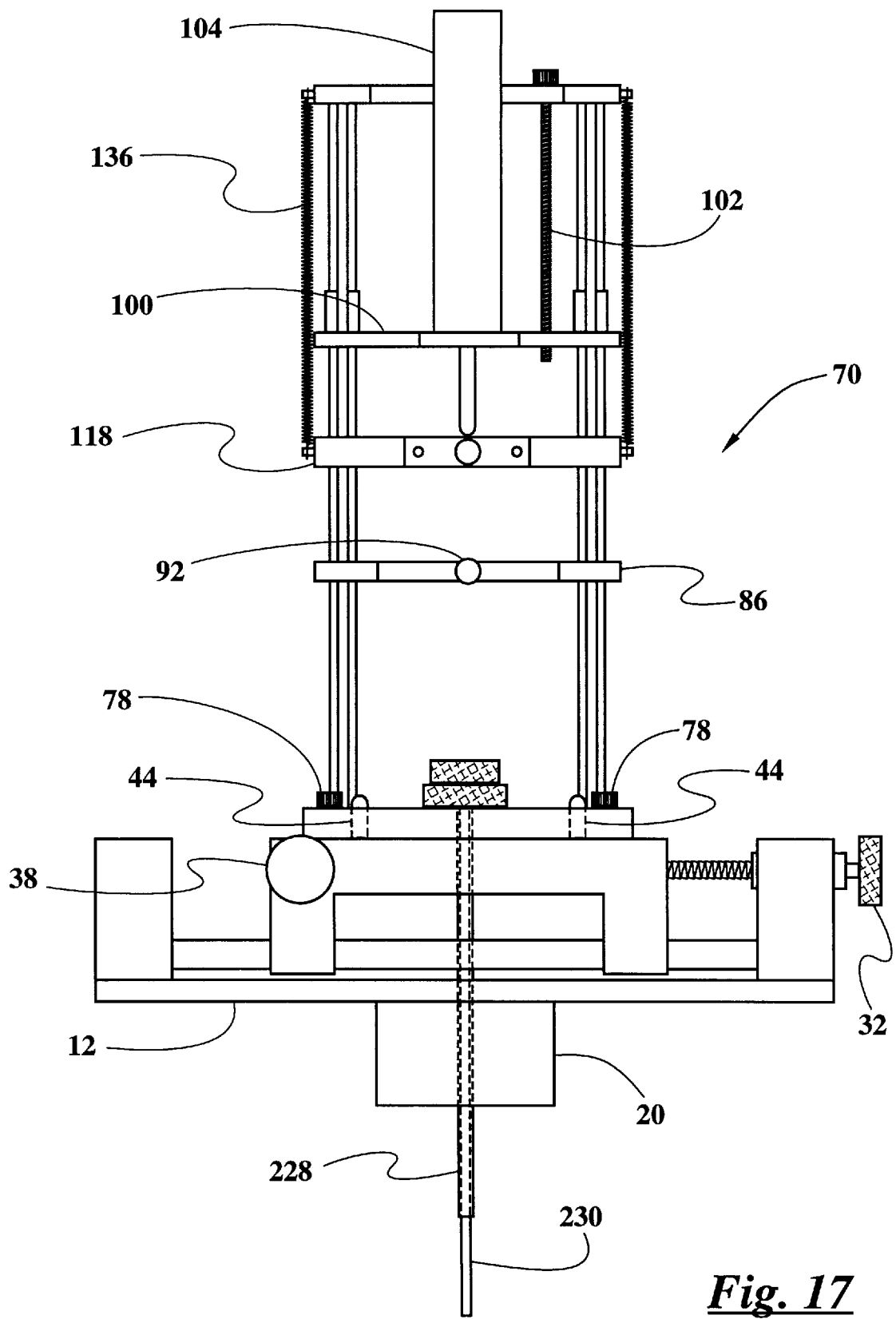
FIG. 17 is an elevation view of the stereotactic guide apparatus of the present invention, comprising the Z-stage of FIG. 10 mounted to the XY-stage of FIG. 1.

FIG. 17 illustrates the Z-stage 70 mounted to the XY-stage 11. The base 72 of the Z-stage 70 is mounted onto the top panel 40 of the Y-slide 36. The upstanding pins 44 on the top panel 40 of the Y-slide 36 are received within the alignment holes 74 in the base 72 of the Z-stage 70. The securing screws 78 in the base 72 of the Z-stage 70 engage the threaded holes 46 in the top panel 40 of the Y-slide 36. Actuation of the medial and anterior movement mechanisms 32, 38 thus not only move the X-slides 30a, 30b and the Y-slide 36 but also move the Z-stage 70 with respect to the X- and Y-axes.

Figure 18:
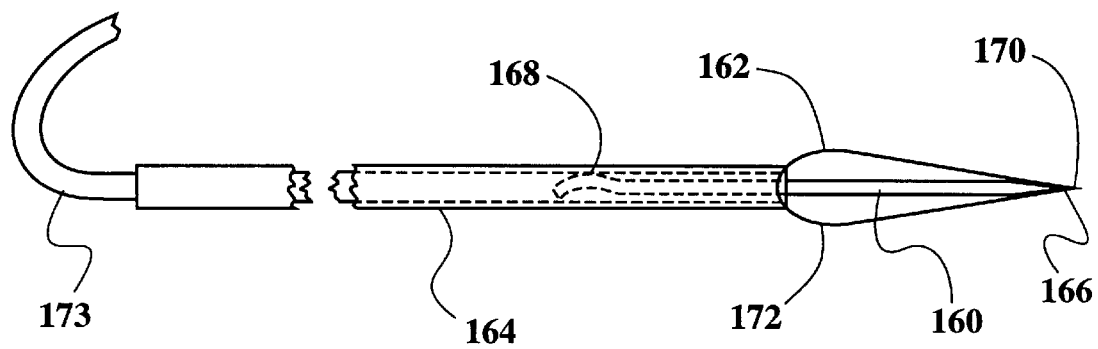
FIG. 18 is a side view of an electrode assembly for use with the stereotactic guide apparatus of FIG. 17.

Referring now to FIG. 18, a novel electrode 150 is disclosed. The electrode 150 comprises a hollow conductive shaft 156, an electrode wire 160, a glass tip 162, and insulation 164. The shaft 156 will typically range from 210 to 300 millimeters in length. The electrode wire 160 tapers to a sharp tip 166 at its forward end. In the disclosed embodiment, the sharp tip 166 is formed by chemically etching the electrode wire 160 in an acid bath. A bend 168 is formed in the rearward end of the electrode wire 160 such that when the rearward end of the electrode wire 160 is inserted into the forward end of the hollow shaft 156, the bend will form an interference fit which retains the electrode wire within the hollow shaft during subsequent manufacturing steps. The glass tip 162 is then formed directly onto the forward end of the shaft 156, encapsulating the portion of the electrode wire 160 which extends forward of the hollow shaft 156. The glass tip 162 tapers to a sharp forward tip 170 substantially coincident with the forward end of the electrode wire 160. A tube of insulating material 164 is then advanced forward over the shaft 156 and over the rearward end of the glass tip 162. Glue is applied at the junction 172 between the insulation and the glass bulb to seal the joint. An electrical lead 173 is attached in conductive communication with the rearward end of the shaft 156 for connecting the electrode 150 to an associated electronic device, such as for mapping electrical activity within a patient's brain.

Use of the apparatus for positioning a surgical instrument along three axes during neurosurgery is accomplished as follows. For purposes of illustration, a procedure will be described in which the stereotactic guide apparatus 10 is used in conjunction with a mapping electrode to map electrical activity within the brain.

The Z-stage 70 of the stereotactic guide apparatus 10 is prepared for use as follows. The microdrive unit 104 is installed onto the coarse drive slide 100 by engaging the externally threaded collar 108 of the microdrive unit with the threaded bore 114 of the coarse drive slide. The carrier tube 95 is then installed onto the carrier tube holder 86 by inserting the hollow shaft 96 of the carrier tube downward through the circular opening 90 of the carrier tube holder 86. The annular collar 98 of the carrier tube 95 fits snugly within the circular opening 90 in the carrier tube holder 86, with the head 97 of the carrier tube resting on the upper surface of the carrier tube holder. The thumbscrew 92 on the carrier tube holder 86 is then tightened to retain the carrier tube 95 in place.

An electrode 150 is now installed onto the electrode slide 118 of the Z-stage 70. The electrical lead 173 and rearward end of the shaft 156 of the electrode 150 are passed upward through the lower end of the carrier tube 95. When the rearward end of the shaft 156 of the electrode 150 exits the upper end of the carrier tube 95, the shaft of the electrode is passed between the electrode holder pressure plate 128 and the forward edge 122 of the electrode slide 118. The shaft 156 of the electrode 150 is positioned within the vertical notch 132 in the face 122 of the electrode slide 118. When the electrode 150 has been advanced to a location in which the glass tip 162 of the forward end of the electrode 150 resides just within the lower end of the carrier tube 95, the thumb screw 130 of the electrode holder assembly 120 is tightened, causing the electrode holder pressure plate 128 to advance toward the forward edge 122 of the electrode slide 118, thereby clamping the shaft 156 of the electrode 150 within the notch 132. The electrical lead 173 is then attached to the positive terminal of a conventional electrode mapping apparatus, and a wire is run between the carrier tube 95 and the negative terminal of the electrode mapping apparatus to complete the connection of the electrode 150.

The XY-stage 11 of the device 10 is prepared for use as follows. The outer guide tube 228 is mounted to the Y-slide 36 by inserting the shaft 234a of the outer guide tube downward through the threaded aperture 42 in the center of the top panel 40 of the Y-slide 36 and then through the hollow cylindrical body 22 of the mounting adapter 20. The externally threaded collar 242a of the outer guide tube 228 is then threaded into the threaded aperture 42 in the Y-slide 36.

The slide 51 is assembled onto the arc 50 of the headframe 49 as follows. The block 64 is coupled to the arc 50 by sliding the arc into the arcuate track 66 formed on the interior surface of the block. The bracket member 52 is then installed onto the block 64 by positioning the block within the channel 60 formed in the forward face 62 of the head portion 58 of the bracket member. The headframe 49 is then mounted to the patient's skull in the conventional manner.

Figure 19:
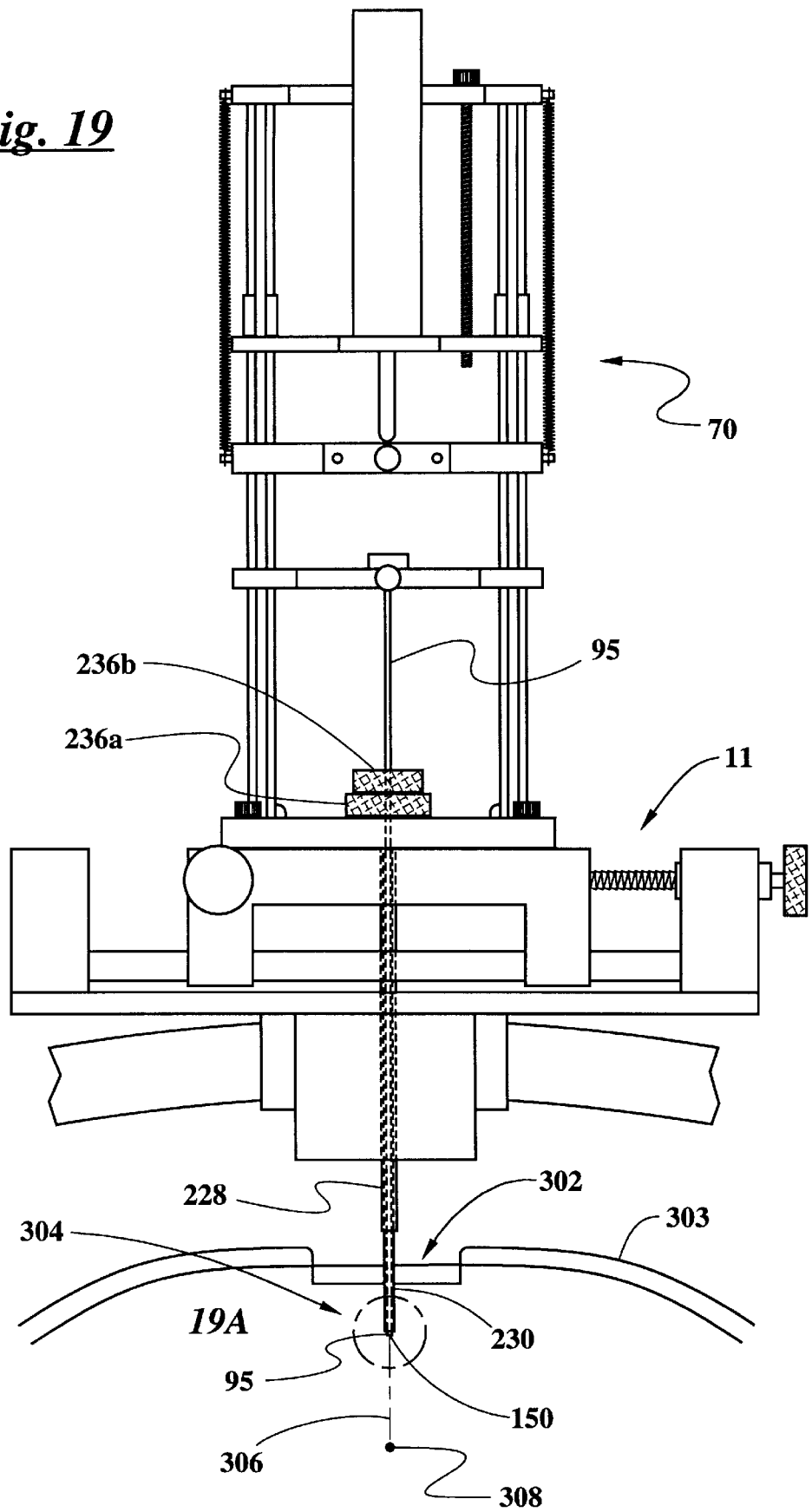
FIG. 19 is a side view showing the stereotactic guide apparatus of FIG. 17 used to perform a neurosurgical procedure.

The XY-stage 11 is then mounted to the arc 50 of the headframe 49 by inserting the cylindrical body 22 of the mounting adapter 20 into the bore 68 of the slide 51. The length of the shaft 234a of the outer guide tube 228 is such that the outer guide tube terminates at a location spaced upward from the patient's skull. The physician can then use the outer guide tube 228 as a bore sight, peering through the outer guide tube to spot the location on the patient's head which is aligned with the axis of the guide tube. To change the location of the outer guide tube 228 to align to a different portion of the patient's head, gross adjustments can be made by moving the slide 51 along the arc 50 of the headframe 49, or by adjusting the arc 50 with respect to the headframe. To make fine adjustments, the medial movement mechanism 32, anterior movement mechanism 38, or both can be actuated to move the outer guide tube 228 in the X-direction, Y-direction, or both. If desired, an elongated marker, e.g., a felt-tip marker, can be inserted through the outer guide tube 228 to mark the location on the patient's skull. As shown in FIG. 19, a burr hole 302 is then made in the patient's skull 303 in the conventional manner to expose the brain 304.

The inner guide tube 230 and stylet 232 are next assembled together and inserted through the outer guide tube 228 into the patient's brain 304, the stylet 232 serving to minimize coring and trauma to the brain tissue during introduction. When the inner guide tube 230 and stylet 232 are fully inserted into the outer guide tube 228, the externally threaded collar 242b of the inner guide tube is threaded into the internal threads 240a of the outer guide tube to couple the outer and inner guide tubes 228, 230 together. The stylet 232 is then withdrawn, by disengaging the externally threaded collar 242c of the stylet 232 from the internal threads 240b of the inner guide tube 230 and extracting the stylet from the inner guide tube.

The Z-stage 70 is then positioned onto the XY-stage 11 as follows. Referring to FIG. 19, the carrier tube 95 and enclosed electrode 150 are fed downward into the upper end of the inner guide tube 230 and advanced through the inner guide tube. The Z-stage 70 is advanced until the base 72 of the Z-stage is positioned onto the Y-slide 36 of the XY-stage 11. The upstanding pins 44 of the Y-slide 36 are received within the alignment holes 74 in the base 72 of the Z-stage 70. The securing screws 78 are then engaged with the threaded holes 46 in the upper surface of the platform 40 of the Y-slide 36 to secure the base 72 of the Z-stage 70 to the Y-slide. As previously indicated, the asymmetrical arrangement of the pins 44 and threaded holes 46 of the XY-stage 11 prevents the Z-stage 70 from accidentally being installed onto the XY-stage improperly.

Figure 19A:
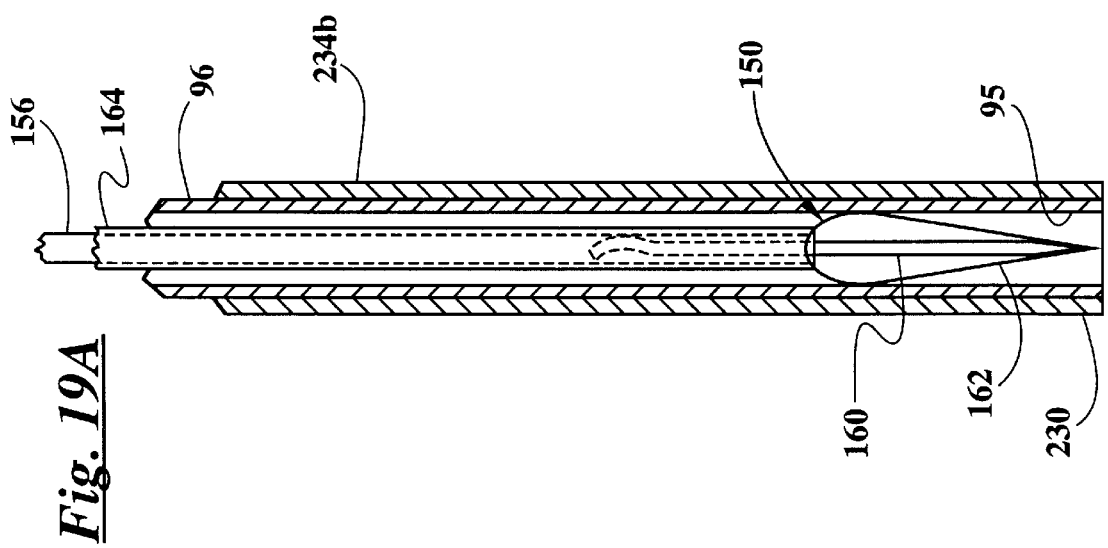
FIG. 19A is an enlarged view of the portion of FIG. 19 indicated by the circle 19A.

As can be seen in the enlarged view of FIG. 19A, when the Z-stage 70 is assembled onto the XY-stage 11, the lower end of the carrier tube 95 is located substantially coincident with the lower end of the inner guide tube 230. The glass tip 162 of the electrode 150 resides just within the forward end of the carrier tube 95.

The Z-stage may now be actuated to advance the electrode 150 downward beyond the lower end of the inner guide tube 130 and into the patient's brain. Lengthy advances of the electrode 150 may be accomplished by means of the coarse drive mechanism 102 on the Z-stage 70, and fine advances of the electrode may be accomplished by means of the microdrive 104. The electrode 150 is advanced along a target line 306 toward a target 308. As the electrode 150 is advanced, whether by the coarse drive mechanism 102 or the microdrive 104, the scale 138 and the linear potentiometer 140 track the displacement of the electrode in the Z-direction.

When it is desired to map a portion of the brain along a different target line, the following procedure is used to reposition the electrode 150 along the X-axis, the Y-axis, or both. First, the electrode 150 is retracted within the carrier tube 95. The Z-stage 70 is then detached and removed from the XY-stage 11 by removing the securing screws 78 from the threaded holes 46 and lifting the Z-stage off of the XY-stage. As the Z-stage 70 is separated from the XY-stage 11, the carrier tube 95 and electrode 150 are withdrawn from the inner guide tube 230.

When the Z-stage 70 has been removed and the carrier tube 95 and electrode 150 have been completely withdrawn from the inner guide tube 230, the inner guide tube is disassembled from the XY-stage 11. The cap 236b of the inner guide tube 230 is rotated to disengage the externally threaded collar 242b of the inner guide tube from the internally threaded bore 240a of the cap 236a of the outer guide tube 228, and the shaft 234b of the inner guide tube 230 is withdrawn from the outer guide tube 228. Since the lower end of the outer guide tube 228 terminates above the patient's skull, it is not necessary to remove the outer guide tube before adjusting the XY-stage.

All portions of the stereotactic guide apparatus 10 which penetrated the patient's brain have now been extracted, and repositioning of the XY-stage 11 is now possible. The XY-stage 11 is relocated along the X-axis, the Y-axis, or both by adjusting the medial movement mechanism 32 and the anterior movement mechanism 38 as appropriate.

When the XY-stage 11 has been repositioned to the desired new location, the inner guide tube 230 and stylet 232 are assembled together as previously described and are reintroduced through the outer guide tube 228. When the threaded collar 242b of the inner guide tube 230 has been coupled to the cap 236a of the outer guide tube 228, the stylet 232 is again withdrawn. The carrier tube 95 and electrode 150 are then reintroduced into the upper end of the inner guide tube 230, and the Z-stage 70 is reassembled onto the XY-stage 11 as hereinabove explained. The electrode 150 is then advanced as previously described to map brain activity along a new target line. The procedure of mapping and repositioning can be repeated as often as necessary until the mapping is completed.

While use of the stereotactic guide apparatus 10 to position a surgical instrument along three axes has been disclosed with respect to a procedure for mapping brain activity, it will be appreciated that the apparatus 10 is equally well suited for other purposes. For example, the apparatus can be used to direct other instruments, such as an RF lesion electrode, a cryogenic lesion electrode, a biopsy needle, or an injection cannula. The apparatus 10 can also be used to perform other types of stereotactic neurosurgery, such as functional neurosurgery, deep brain microstimulation, brain mapping, and treating Parkinson's disease, epilepsy, sleep disorders, movement disorders, pallidotomies, and thalimotonies.

It will be appreciated by those skilled in the art that the use of a mapping electrode 150 advantageously involves the use of the carrier tube 95 because the mapping electrode 150 is quite thin and has very little structural rigidity. Without the carrier tube 95, it would be difficult to advance the considerable length of the electrode downward through the inner guide tube 230. However, it will also be appreciated that other types of electrodes, for example, lesion electrodes of either the RF or cryogenic varieties, and needles such as biopsy needles or injection cannulae, are more structurally rigid and hence can be used directly within the inner guide tube without an associated carrier tube.

Figure 20:
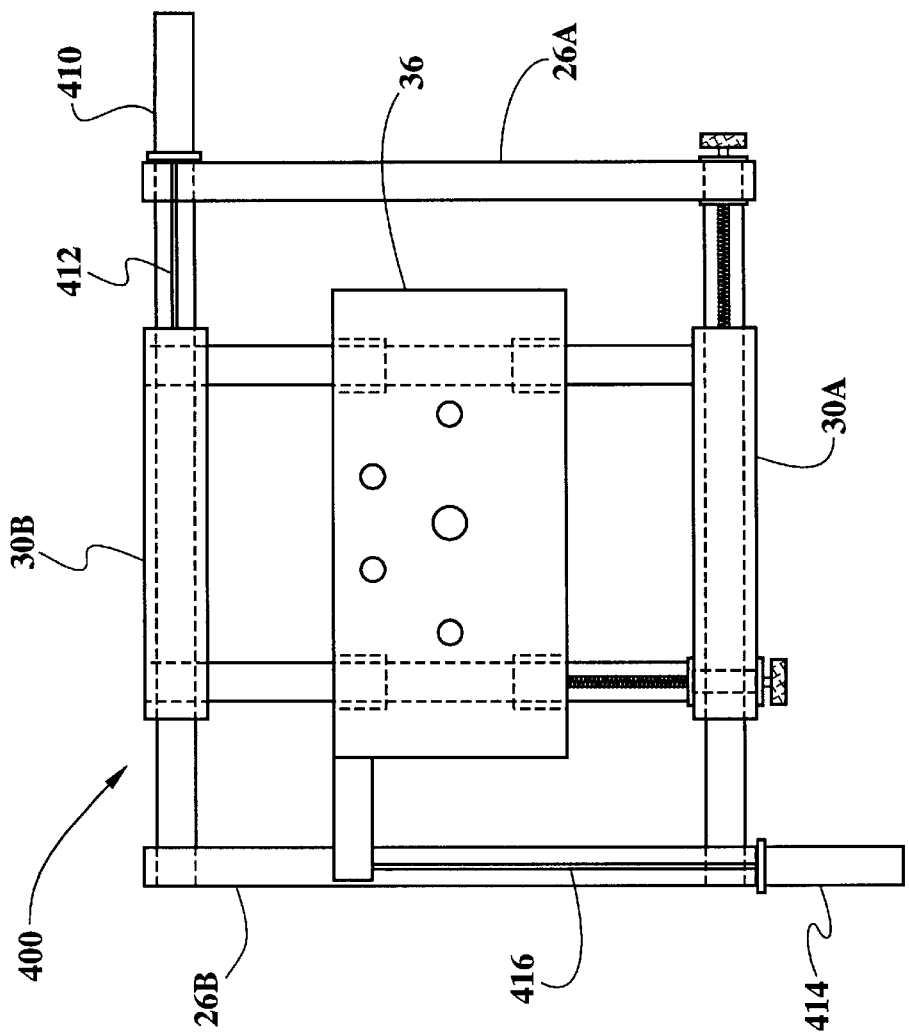
FIG. 20 shows an alternate embodiment of an XY-stage.

FIG. 20 shows an alternate embodiment of an XY-stage 400 which provides electronic means for tracking the displacement of an electrode in the X and Y directions. A first linear potentiometer 410 is fixedly mounted to the support 26a, and a potentiometer push rod 412 extending from the potentiometer is coupled to the X-slide 30b. A second linear potentiometer 414 is fixedly mounted to the support 26b and has a potentiometer push rod 416 coupled to the Y-slide 36. Displacement of the electrode in the X-direction will be detected by the first linear potentiometer 410, while displacement of the electrode in the Y-direction will be detected by the second linear potentiometer 414.

The XY-stage 11, as illustrated in FIGS. 1 and 2, can be used independently of the headframe 49 wherein the assembly is secured onto the head or skull of a mammal for research, chronic recording, or the like. Optionally the XY-stage 11 can be used in combination with a conventional headframe independently of the Z-stage 70, where guidance or control of the surgical instrument is desired in only the X direction, Y direction, or both.

Figure 21:
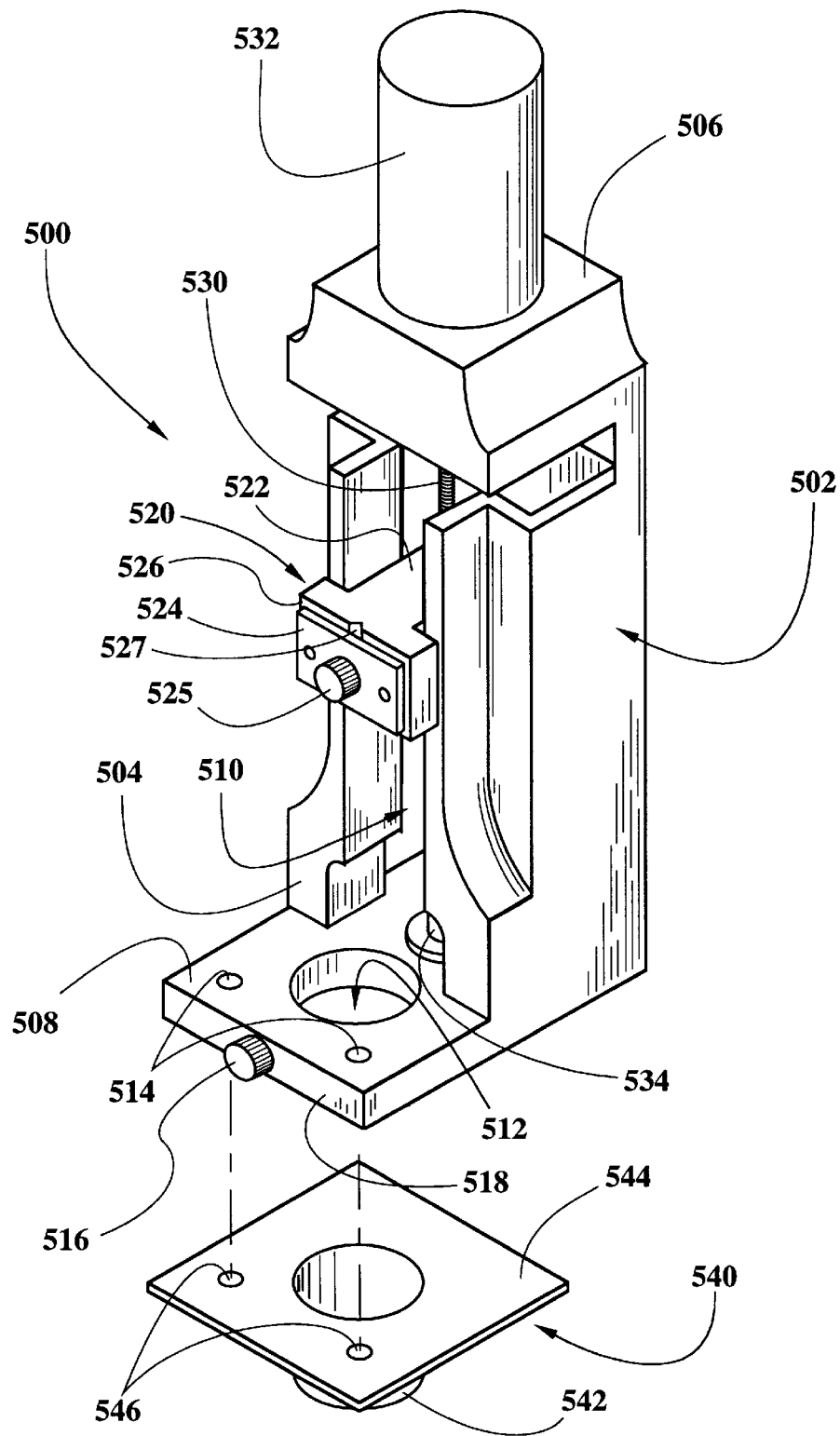
FIG. 21 is a perspective view of an alternate embodiment of a Z-stage.

Referring now to FIG. 21, an alternate embodiment of a Z-stage 500 is shown. The Z-stage 500 comprises a housing 502 having a front 504, a top 506, and a base 508. A track 510 is formed in the front 504 of the housing 502.

The base 508 defines a circular opening 512 and a pair of alignment holes 514 therein. A thumb screw 516 is threadably mounted to the forward edge 518 of the base 508 and has a tip 519 (FIG. 23) which extends radially into the circular opening 512.

Figure 23:
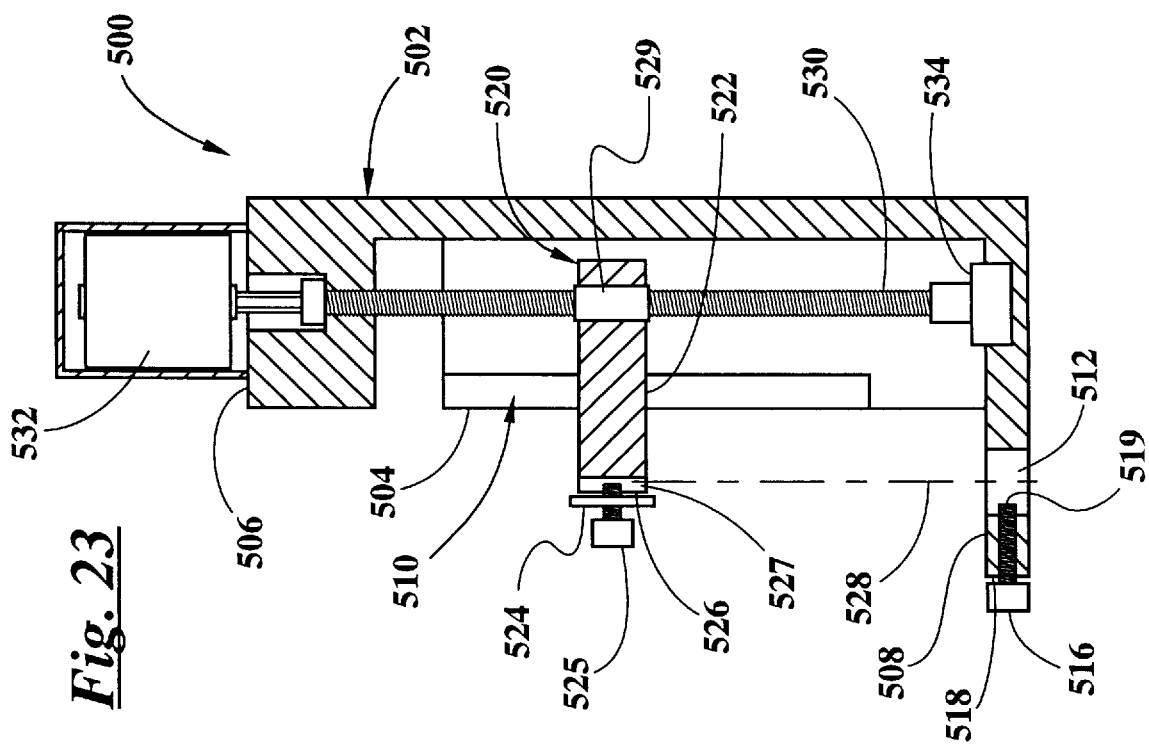
FIG. 23 is a side cut-away view taken along line 23—23 of FIG. 22.
Figure 22:
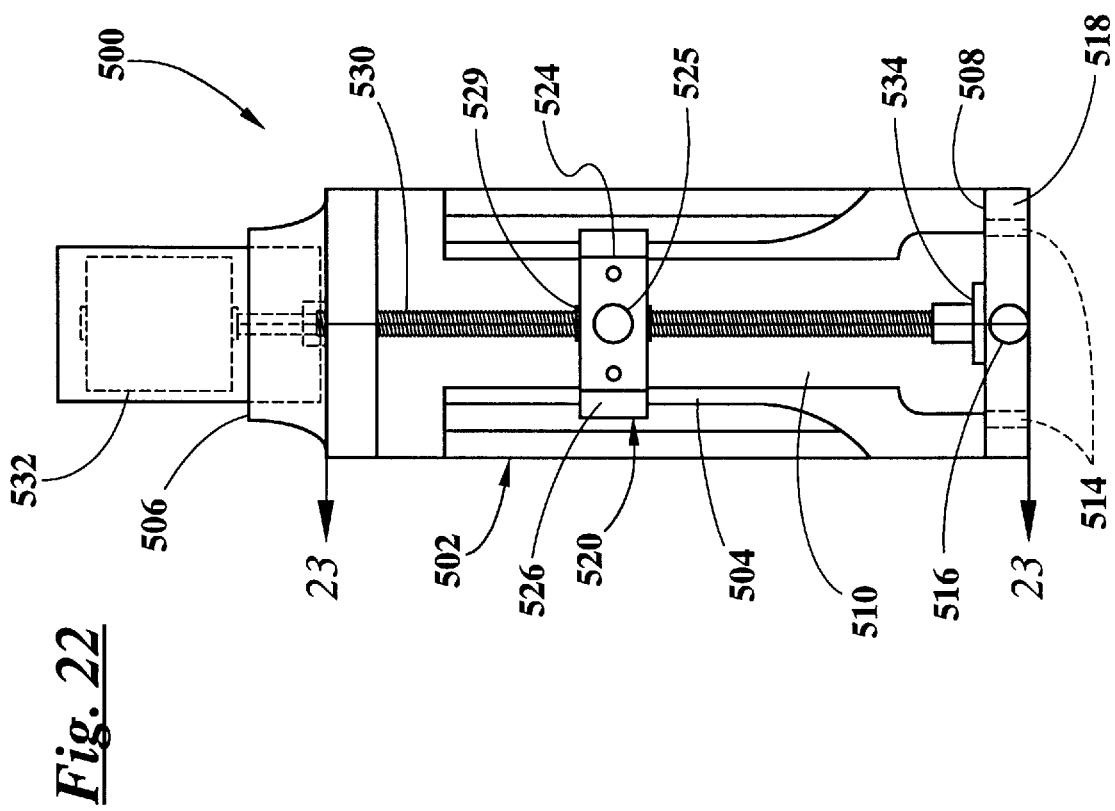
FIG. 22 is a front view of the apparatus of FIG. 21.

A slide block 520 is slidably mounted within the housing 502 and has a nose portion 522 which slides within the track 510 in the front 504 of the housing. An instrument pressure plate 524 with holding screw 525 is mounted to the front face 526 of the slide block 520. A vertical notch 527 is formed in the front face 526 of the slide block 520. The vertical notch 527 is vertically aligned with the circular opening 512 in the base 508, as shown by the line 528 (FIG. 23). A vertically oriented threaded bushing 529 (FIGS. 22, 23) is located within a back central portion of the slide block 520.

A turn screw 530 is vertically mounted within the housing and engages the threaded bushing 529 in the slide block 520. A motor 532 is mounted to the top 506 of the housing 502 and is coupled, either directly or through a suitable gear mechanism, to the upper end of the turn screw 530. A rotary encoder 534 is mounted to the base 508 of the housing 502, and the lower end of the turn screw 530 is coupled to the rotary encoder.

The Z-stage 500 further comprises a tubular mounting adapter 540 analogous to the adapter 20 of the previously described embodiments. The adapter 540 includes a hollow tubular body 542 and has a flange 544 formed at its upper end. The adapter 540 further includes a pair of threaded bores 546. When the adapter 540 is mounted to the bottom of the base 508 of the housing 502, the hollow tubular body 542 of the adapter aligns with the circular opening 512 in the base, and the threaded bores 546 in the adapter align with the alignment holes 514 in the base of the housing. A pair of screws can be inserted through the alignment holes 514 in the base 508 and threaded into the bores 546 of the mounting adapter 540 to secure the housing 502 to the adapter.

To mount the Z-stage 500 to a headframe 49 (FIG. 7), the mounting adapter 540 is secured to the bottom of the base 508 of the housing 502. The hollow tubular body 542 of the mounting adapter 540 then couples to the circular bore 68 in the L-shaped bracket member 52 of the arc slide 51 (FIGS.

8 and 9) in the same manner hereinabove described with respect to the adapter 20.

The Z-stage 500 is prepared for use as follows. A carrier tube 95 (FIG. 16) is installed onto the base 508 of the housing 502 by inserting the hollow shaft 96 of the carrier tube downward through the circular opening 512 of the base. The annular collar 98 of the carrier tube 95 fits snugly within the circular opening 512 in the base 508, with the head 97 of the carrier tube resting on the upper surface of the base. The thumbscrew 526 on the base 508 is then tightened to retain the carrier tube 95 in place.

An electrode 150 (FIG. 18) is now installed onto the electrode slide 118 of the Z-stage 500. The electrical lead 173 and rearward end of the shaft 156 of the electrode 150 are passed upward through the lower end of the carrier tube 95. When the rearward end of the shaft 156 of the electrode 150 exits the upper end of the carrier tube 95, the shaft of the electrode is passed between the instrument pressure plate 524 and the front face 526 of the slide block 520. The shaft 156 of the electrode 150 is positioned within the vertical notch 527 in the front face 526 of the slide block 520. When the electrode 150 has been advanced to a location in which the glass tip 162 of the forward end of the electrode 150 resides just within the lower end of the carrier tube 95, the holding screw 525 of the slide block 520 is tightened, causing the instrument pressure plate 524 to advance toward the front face 526 of the slide block 520, thereby clamping the shaft 156 of the electrode 150 within the vertical notch 527. The electrical lead 173 is then attached to the positive terminal of a conventional electrode mapping apparatus, and a wire is run between the carrier tube 95 and the negative terminal of the electrode mapping apparatus to complete the connection of the electrode 150.

To move the electrode along the Z-axis, the motor 532 is actuated to drive the turn screw 530. Since the slide block 520 is prevented from rotating by its fit within the housing 502, the turn screw 530 rotates within the threaded bushing 529. This rotation moves the slide block 520 upward or downward, depending upon the direction of rotation of the turn screw 530. The rotary encoder 534 tracks the vertical location of the slide block 520, and hence the attached electrode 150, by counting the rotations of the turn screw 530.

The Z-stages 70, 500 can each be used in conjunction with an X-Y stage 11, 400, or can be mounted directly to the arc slide 51 of the headframe 49 where control of an instrument only along the Z-axis is needed. In addition, while the Z-stages 70, 500 have been disclosed with respect to mapping electrodes, it will be understood that other types of electrodes, and any type of surgical instrument which is moved along a Z-axis, can be mounted to the Z-stage.

Finally, it will be understood that the preferred embodiment has been disclosed by way of example, and that other modifications may occur to those skilled in the art without departing from the scope and spirit of the appended claims.

What is claimed is:

1. A stereotactic guide apparatus for use with a neurosurgical headframe comprising an arc extending above and across the skull of a patient to whom the headframe is mounted and a slide mounted for sliding movement along said arc, said stereotactic guide apparatus comprising:

a platform defining a plane, said platform having an X-axis extending in a first direction within said plane, a Y-axis extending in a second direction within said plane perpendicular to and intersecting said X-axis, and a Z-axis projecting normal to said plane and through the intersection of said X-axis and said Y-axis;

means for mounting said platform to a slide mounted for sliding movement along an arc of a neurosurgical headframe;

a Z-stage base mounted to said platform;

a Z-axis support means mounted to said Z-stage base and extending parallel to said Z-axis;

instrument slide means movably mounted to said Z-axis support means and movable parallel to said Z-axis; and instrument attachment means operatively associated with said instrument slide means for attaching a surgical instrument to said instrument slide means;

said instrument attachment means and said instrument slide means being arranged such that when a surgical instrument is attached to said instrument slide means and said instrument slide means is moved parallel to said Z-axis, said surgical instrument is advanced through a tubular instrument guide.

2. The stereotactic guide apparatus of claim 1, wherein said Z-stage further comprises:

drive support means fixedly mounted on said Z-axis support means; and drive means operatively associated with said drive support means and said instrument slide means for moving said instrument slide means along said Z-axis support means.

3. The stereotactic guide apparatus of claim 2, wherein said drive means for moving said instrument slide means along said Z-axis support means comprises a turn screw, and wherein said stereotactic guide apparatus further comprises a rotary encoder coupled to said turn screw for detecting displacement of said instrument slide means along said Z-axis.

4. The stereotactic guide apparatus of claim 1, wherein said Z-stage further comprises:

carrier tube support means fixedly mounted on said Z-axis support means; and carrier tube means mounted to said carrier tube support means coaxial with said tubular instrument guide for providing structural support to a surgical instrument attached to said instrument slide means.

5. The stereotactic guide apparatus of claim 1, further comprising Z-axis displacement detection means operatively associated with said Z-axis support means and said instrument slide means for detecting displacement of said instrument slide means along said Z-axis.

6. The stereotactic guide apparatus of claim 5, wherein said Z-axis displacement detection means comprises:

linear scale means mounted to said Z-axis support means; and a reference mark on said instrument slide means in cooperative relation with said linear scale means for indicating the displacement of said instrument slide means along said Z-axis.

7. The stereotactic guide apparatus of claim 5, wherein said Z-axis displacement detection means comprises a linear potentiometer having a housing and a push rod, said housing being operatively associated with one of said Z-axis support means and said instrument slide means, and said push rod being operatively associated with the other of said Z-axis support means and said instrument slide means for electronically detecting displacement of said instrument slide means along said Z-axis.

* * * * *